United States Patent
Spear et al.

(10) Patent No.: US 10,721,333 B2
(45) Date of Patent: Jul. 21, 2020

(54) INTEGRATED SYSTEM FOR PRODUCING PROCEDURAL DATA CHANGE SETS COMMUNICATED TO MULTIPLE CLIENT DEVICES

(71) Applicant: TeleTracking Technologies, Inc., Pittsburgh, PA (US)

(72) Inventors: Steve Spear, Lindstrom, MN (US); Toni D. Morrison, Pittsburgh, PA (US); Corey Paracca, South Park, PA (US); Ann M. Della Porta, East Norriton, PA (US)

(73) Assignee: TeleTracking Technologies, Inc., Pittsburgh, PA (US)

( * ) Notice: Subject to any disclaimer, the term of this patent is extended or adjusted under 35 U.S.C. 154(b) by 339 days.

(21) Appl. No.: 15/142,712

(22) Filed: Apr. 29, 2016

(65) Prior Publication Data
US 2016/0323417 A1   Nov. 3, 2016

Related U.S. Application Data

(60) Provisional application No. 62/155,245, filed on Apr. 30, 2015.

(51) Int. Cl.
*H04L 29/08* (2006.01)
*G16H 10/60* (2018.01)
(Continued)

(52) U.S. Cl.
CPC ............ *H04L 67/36* (2013.01); *G06Q 10/06* (2013.01); *G06Q 10/10* (2013.01); *G16H 10/60* (2018.01);
(Continued)

(58) Field of Classification Search
CPC ......... H04L 67/36; H04L 67/42; H04L 67/10; G16H 10/60
See application file for complete search history.

(56) References Cited

U.S. PATENT DOCUMENTS

| 5,734,898 A | * | 3/1998 | He | ............................ G06F 9/52 |
| 2008/0221924 A1 | * | 9/2008 | Ilkin | ...................... G06Q 10/10 705/2 |

(Continued)

FOREIGN PATENT DOCUMENTS

WO   WO-03025703 A2 *  3/2003  ............. G16H 40/20

OTHER PUBLICATIONS

Search Report for European Patent Application No. EP16167624, dated Aug. 11, 2016, 2 pages, The Hague, Netherlands.
(Continued)

*Primary Examiner* — Chris Parry
*Assistant Examiner* — Steven C Nguyen
(74) *Attorney, Agent, or Firm* — Ference & Associates LLC

(57) ABSTRACT

An embodiment provides a method, including: receiving, at a server, change data from a mobile device; identifying, using a processor, a set of display elements impacted by the change data, wherein said set of display elements comprises display elements of at least two different end user application displays; updating, using the processor, the set of display elements according to the change data; storing, in a memory device, a sequential identification associated with the updated set of display elements; receiving, at the server, a request from an end user client for updated information, wherein the request includes a previous sequential identification; determining, using the processor, a delta representing the difference between the sequential identification and the previous sequential identification; generating, using the pro-
(Continued)

cessor, a set of updated view components for the end user client based on the delta; and communicating, over a network connection, the set of view components to the end user client. Other embodiments are described and claimed.

20 Claims, 5 Drawing Sheets

(51) Int. Cl.
H04L 29/06 (2006.01)
G16H 40/20 (2018.01)
G06Q 10/06 (2012.01)
G06Q 10/10 (2012.01)

(52) U.S. Cl.
CPC ............ *G16H 40/20* (2018.01); *H04L 67/02* (2013.01); *H04L 67/10* (2013.01); *H04L 67/42* (2013.01)

(56) References Cited

U.S. PATENT DOCUMENTS

| | | | | |
|---|---|---|---|---|
| 2008/0306759 | A1* | 12/2008 | Ilkin | G06Q 10/10 705/2 |
| 2013/0325508 | A1* | 12/2013 | Johnson | G06F 19/3418 705/3 |
| 2014/0058779 | A1 | 2/2014 | Kissoon et al. | |
| 2014/0164011 | A1 | 6/2014 | Guelich et al. | |
| 2014/0280605 | A1* | 9/2014 | Zhang | H04L 67/1095 709/205 |
| 2014/0292490 | A1* | 10/2014 | Butler | G06K 7/0008 340/10.1 |
| 2015/0310659 | A1 | 10/2015 | Spear et al. | |
| 2016/0180032 | A1* | 6/2016 | Rovnan | G06F 19/327 705/2 |
| 2016/0239778 | A1* | 8/2016 | Suneja | G06Q 10/06316 |

OTHER PUBLICATIONS

Mesbah et al., "A component- and push-based architectural style for AJAX applications", Journal of Systems and Software, Dec. 1, 2008, 16 pages, Elsevier North Holland, New York, New York.

"Version Control with Subversion, 2nd Edition", Fundamental Concepts, Sep. 23, 2008, 6 pages, O'Reilly Media, Inc.

Extended Search Report for European Patent Application No. EP17195403, dated Oct. 30, 2017, 2 pages, The Hague, Netherlands.

Carlyle, B., "Semantic Delta Encoding with HTTP draft-carlyle-sem-delta-encoding-00", Internet Engineering Task Force, IETF; Standard Working Draft, Internet Society (ISOC) 4, Rue Des Falaises CH-1205 Geneva, Switzerland, Jun. 30, 2012, pp. 1-19.

Collins-Sussman et al., "Chapter 1, Chapter 2" in "Version Control with Subversion, 2nd Edition", O'Reilly Media Inc., Sep. 23, 2008, pp. 1-46.

* cited by examiner

INTEGRATED SYSTEM FOR PRODUCING PROCEDURAL DATA CHANGE SETS COMMUNICATED TO MULTIPLE CLIENT DEVICES

CROSS REFERENCE TO RELATED APPLICATIONS

This application claims priority to U.S. Provisional Application Ser. No. 62/155,245, filed on Apr. 30, 2015, the contents of which are incorporated by reference herein.

BACKGROUND

Disparate client devices, e.g., smart phones, computer work terminals, smart-TVs or other displays, etc., need to be apprised of real-time status changes in workflows. Conventional techniques for accomplishing this include making phone calls or otherwise communicating change information directly. Moreover, some conventional approaches include manual entries into stand alone systems, e.g., provided at a work station, manually writing updates to a whiteboard, etc.

Managing workflows however requires a solution that can maximize both throughput and the fixed costs attributed to the unit of operation. Most of existing inefficiencies in these areas are related to poor communication and communication of data that is not transparent to the interdisciplinary teams working to support the workflow.

Existing electronic records and static scheduling programs are of value; however, the information they document is often historic, static and (if updated) not provided or communicated in real time. Thus, existing systems do not anticipate schedule changes and/or track the workflow and procedural milestone processes in real-time, e.g., on the day of a procedure. Such difficulties are complicated by the modular nature of electronic records and scheduling systems, i.e., these modular units are traditionally not designed to operate in a coordinated fashion. Electronic records, static scheduling programs and the like thus lack any real time transparency to all events relating to a particular workflow.

BRIEF SUMMARY

In summary, one embodiment provides a method, comprising: receiving, at a server, change data from a mobile device; identifying, using a processor, a set of display elements impacted by the change data, wherein said set of display elements comprises display elements of at least two different end user application displays; updating, using the processor, the set of display elements according to the change data; storing, in a memory device, a sequential identification associated with the updated set of display elements; receiving, at the server, a request from an end user client for updated information, wherein the request includes a previous sequential identification; determining, using the processor, a delta representing the difference between the sequential identification and the previous sequential identification; generating, using the processor, a set of updated view components for the end user client based on the delta; and communicating, over a network connection, the set of view components to the end user client.

Another embodiment provides a system, comprising: an application server comprising a memory device; and a network communication device; said server including a processor configured to: receive change data from a mobile device; identify a set of display elements impacted by the change data, wherein said set of display elements comprises display elements of at least two different end user application displays; update the set of display elements according to the change data; store, in the memory device, a sequential identification associated with the updated set of display elements; receive a request from an end user client for updated information, wherein the request includes a previous sequential identification; determine a delta representing the difference between the sequential identification and the previous sequential identification; generate a set of updated view components for the end user client based on the delta; and communicate, using the network communication device, the set of view components to the end user client.

A further embodiment provides a program product, comprising: a storage device having code stored therein that is executable by a processor, the code comprising: code that receives, at a server, change data from a mobile device; code that identifies, using a processor, a set of display elements impacted by the change data, wherein said set of display elements comprises display elements of at least two different end user application displays; code that updates, using the processor, the set of display elements according to the change data; code that stores, in a memory device, a sequential identification associated with the updated set of display elements; code that receives, at the server, a request from an end user client for updated information, wherein the request includes a previous sequential identification; code that determines, using the processor, a delta representing the difference between the sequential identification and the previous sequential identification; code that generates, using the processor, a set of updated view components for the end user client based on the delta; and code that communicates, over a network connection, the set of view components to the end user client.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
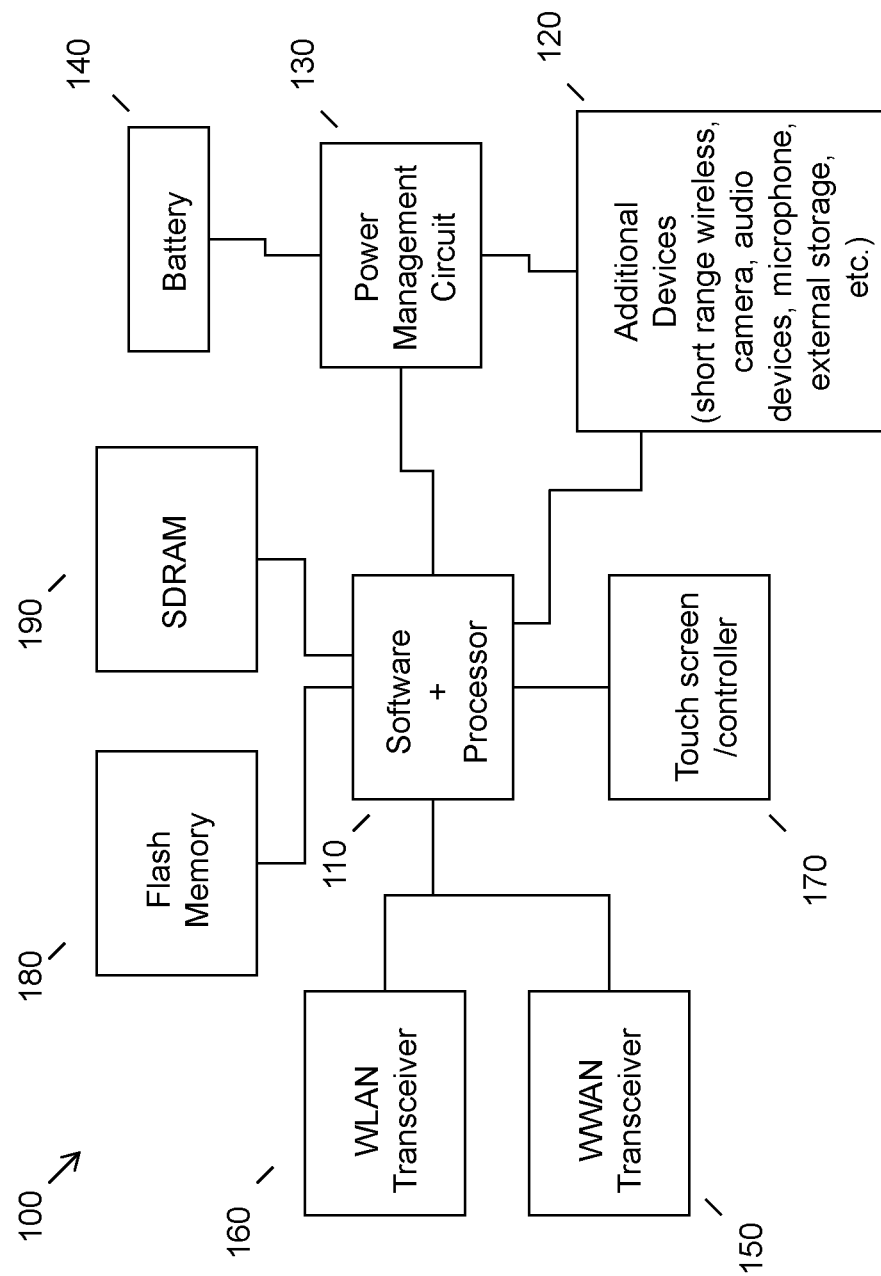
FIG. 1 illustrates an example of information handling device circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well known structures, materials, or operations are not shown or described in detail to avoid obfuscation.

An embodiment provides centrally managed workflow service, implemented for example in a server or servers that are connected to other, existing systems (e.g., patient or asset RTLS tracking systems, bed management systems, scheduling systems, etc.) or that operate in a stand-alone implementation. A central service paradigm offers coordinated communication to various health care staff and permits a central location that may be updated with change information that is distributed to various clients, e.g., mobile devices, client workstations or other linked systems of devices.

In an embodiment, a screen or view approach is provided such that, for a given service, e.g., a surgical clinic, a heart clinic, an orthopedic clinic, a cancer clinic, ambulatory clinic(s), allergy and testing clinics, an infusion clinic, radiology or imaging clinics, a pharmacy clinic, etc., a series or set of views offers staff, management and even patients visible data and information that permits real time tracking and progress information as a patient enters the service, proceeds through the service, and is discharged from the service or transitioned to another service, e.g., another clinic, a pharmacy on site, etc. The quality of the data and information is improved via central management, as various sources may be used to update the views or screens, in real time, as accessed by a central manager. By way of example, a central server may access existing scheduling data and electronic medical record (EMR) data to initially populate a screen or view, e.g., a screen or view offering a view of the day's scheduled patients, their procedures, the units or areas to which they are assigned, and when, the health care staff assigned to work with the units, areas and patients, etc.

By implementing a centrally coordinated system paradigm, an embodiment facilitates coordination and distribution of the best available information in a timely fashion. Thus, an embodiment may update initially scheduled times, communicate delays or other information (e.g., alerts) to the various views or screens such that users may be apprised of updates in real time. This facilitates efficient use of resources and keeps health care staff, managers and patient family members apprised of the actual progression of the patient(s) through the work flow(s).

The screens or views offer the client devices the ability to view and in some cases update (e.g., depending on the user's role) the information that is currently available in the system. By way of example, a health care staff member currently with the patient, e.g., in preoperative care area, may provide an update (e.g., via mobile application, desktop web browser interface or the like) such that a delay in the patient's progress to the operating room is communicated to the central manager. The central manager in turn may provide update(s), e.g., notification of the delay, to other devices, e.g., by communicating information allowing the screens or views of the client devices to be changed.

The screens or views are implemented with specific functionality. For example, a screen or view allows a user to be apprised of delays (detected manually, e.g., by staff input, or automatically, e.g., by missing RLTS milestone data, etc.) in a view via use of a timer icon. Other icons and supporting functionality are provided, and these may be customized according to the work flow in question. A screen or view also permits authorized users, e.g., healthcare staff, to implement changes to the workflow (e.g., indicate patient delays, indicate early completion of various tasks, indicate changes in the availability of certain staff members, indicate changes in the availability of certain units, areas or pods, etc.). This may be implemented via use of a drag and drop or other interface functionality supported by executable code associated with the screen or view.

Given the centrally managed approach described herein, an embodiment facilitates generation of reports that leverage the most up to date, accurate and granular data available. Thus, an embodiment may be preprogrammed to generate standard reports from EMR data, scheduled data, and/or actual work flow completion data, and may be customized to access data of the centrally managed systems and/or other systems to generate custom reports.

An embodiment enhances the EMR and other systems (e.g., scheduling, real time tracking, etc.) by integrating their data into a series of useful screens or views for particular health care staff members. For example, an embodiment takes an anticipated schedule and tracks the patient flow and procedural milestone processes in real-time on the day of the procedure. This provides real time transparency to all events relating to patients, locations and treatment staff. By communicating activities as they are happening, an embodiment supports effective in-the-moment decision making to minimize the many unanticipated changes that invariably occur throughout the day and provide staff the ability to make changes. An embodiment therefore provides an integrated system similar to an "air traffic control system"—one that can not only locate and track a patient, but also all the care providers and assets that are involved in patient care. Additionally, an embodiment may use real time data to highlight (e.g., visually) anticipated gaps, overlaps or other status indicators that affect one or more patient, treatment unit, staff member or asset.

Orchestrating resources and having visual screens displaying updated data provides a "window" into operating/procedure rooms and ensures all stakeholders, including families, are informed, leading to reduced variability in the health care delivery system. This seamless care coordination across settings positively impacts patient safety, improves patient outcomes and helps organizations drive efficiency.

An embodiment provides a procedural patient throughput solution that enables enhanced patient throughput and increases utilization of high touch, high volume procedural and therapy areas including: the perioperative suite/surgical department, ambulatory/outpatient surgery centers (ASC's), procedural areas (catheterization lab, GI lab, including areas providing multiple procedures—both inpatient and outpatient) and other ancillary areas of the hospital.

An embodiment may be integrated as a module for management system (e.g., included as a module along with modules for pre-admission tracking, electronic bed board, transport tracking, and/or bed tracking) or an embodiment may be provided as a stand-alone procedural patient throughput system. An embodiment works collaboratively with the various aspects of the existing system(s) to provide a comprehensive end-to-end picture of the patient flow continuum within the hospital or health system.

An embodiment is effective in higher complexity workflows such as perioperative or minimally invasive procedures (in a hospital or ambulatory setting), catheterization labs, endoscopy, interventional radiology, interventional neurology, cardio-vascular labs, etc., which are performed by one or multiple health care personnel. These procedures can entail discrete or multiple workflows and are typically scheduled in advance. In facilities where these areas are intertwined with diagnostic imaging and/or labs, an embodiment provides an excellent solution for the whole suite of activities. Facilities having care areas are intertwined with diagnostic imaging and/or labs are quite common, especially in ambulatory facilities.

An embodiment may also be employed for visualizing and managing medium complexity work flows such as pediatric MRI services, EKG services, hemo-dialysis services, perinatal services, and electrophysiology procedures. The medium complexity areas may have multiple procedure rooms with equipment varying by procedure type. Some medium complexity areas may have preparation locations used before the procedure and recovery locations for after the procedure. The healthcare staff caring for the patient in each area is often limited to one or two, whereas the steps performed in each area are often limited to two or three steps.

An embodiment may be employed as well as in low complexity work flows such as radiology services (X-ray, MRI, CT scans), ultrasound services, nutrition services, sleep labs, physical therapy services, etc. These low complexity areas provide in and out visits and/or procedures. These low complexity areas often do not require the coordination of a large number of staff and may have only one or two tracked procedure steps (e.g., start and complete). Procedure staff for such services may be scheduled or assigned on an ad-hoc basis or may not require individual staff to be assigned unless a specific issue arises. Coordination of such low complexity services itself becomes complex throughout a larger facility with numerous rooms or when low workflow procedural areas interact with higher workflow areas, e.g., a pharmacy work flow may be part of a more complex work flow, e.g., in patient surgery work flow.

In an embodiment, the system is integrated with a real time location service (RTLS) for automated tracking and updates (e.g., patient flow updates) and therefore may be integrated with various modules or systems, e.g., a transport tracking system. This facilitates automated information influx into the central system and to the various screens or views of the clients.

An embodiment also provides automated production of standard reports, e.g., for the operating room (OR), whereas previously users had to create their own reports using custom views and techniques. The reports may be based on and reflect data gathered from various systems. For example, a report may be automatically generated to show average patient throughput times for various areas of a hospital or treatment facility, summarize delay points, and highlight problem areas for improvement, etc. Additionally, an embodiment includes standard templates and reports for ambulatory facilities, in addition to the already existing templates that may be provided with the system.

The illustrated example embodiments will be best understood by reference to the figures. The following description is intended only by way of example, and simply illustrates certain example embodiments.

While various other circuits, circuitry or components may be utilized in information handling devices, with regard to system on chip circuitry, an example illustrated in FIG. 1 includes a system 100 on a chip or circuit design found for example in tablets, smart phones or other mobile computing platforms. Software and processor(s) are combined in a single chip or circuit 110. Processors comprise internal arithmetic units, registers, cache memory, busses, I/O ports, etc., as is well known in the art. Internal busses and the like depend on different vendors, but essentially all the peripheral devices (120) may attach to a single chip or circuit 110. The circuitry 100 combines the processor, memory control, and I/O controller hub all into a single chip 110. Also, a system 100 of this type does not typically use SATA or PCI or LPC. Common interfaces, for example, include SDIO and I2C.

There are power management chip(s) or circuit(s) 130, e.g., a battery management unit, BMU, which manage power as supplied, for example, via a rechargeable battery 140, which may be recharged by a connection to a power source (not shown). In at least one design, a single chip or circuit, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additional devices 120 may be included, for example external storage. Commonly, system 100 will include a touch screen 170 for data input and display/rendering. System 100 also typically includes various memory devices, for example flash memory 180 and SDRAM 190.

Information handling device circuitry, as for example outlined in FIG. 1, may be used in mobile client devices such as a smart phone that provide and receive updates or in a server or system that coordinates with various systems, i.e., receiving various change information and coordinating the communication of the same. As will be appreciated by one having ordinary skill in the art, other circuitry or additional circuitry from that outlined in the example of FIG. 1 may be employed in various electronic devices that are used in whole or in part to implement the systems, methods and products of the various embodiments described herein.

Figure 2:
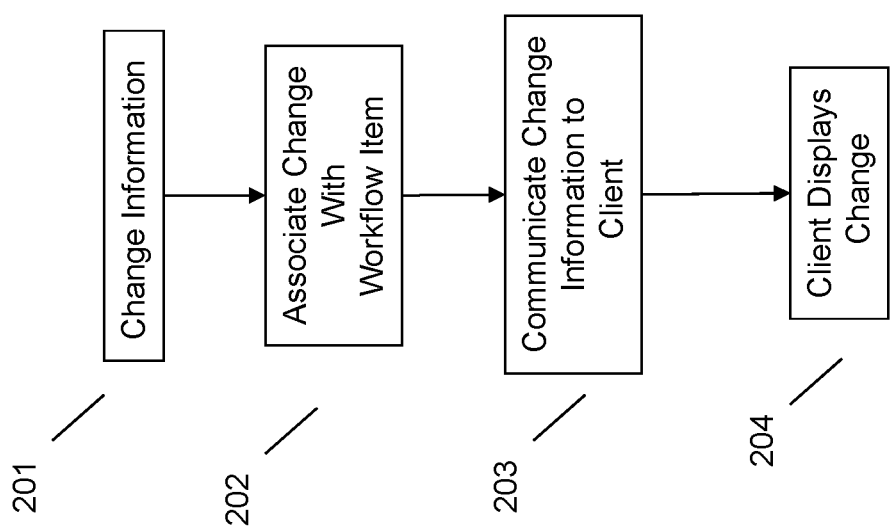
FIG. 2 illustrates an example method of communicating change data for a client screen or view.

Referring to FIG. 2, an example of change information is input to a central server at 201. This may correspond for example to a staff member updating information, e.g., at a workstation or via a mobile application, e.g., a surgeon checking into a particular operating room, data obtained from an RTLS system, etc. Additional sources of change information may include but are not necessarily limited to data from an existing or legacy system, e.g., a scheduling system, an EMR system, etc.

At the central server, the change information is associated with appropriate workflow items at 202. For example, surgeon check in information may be used to identify the surgeon's workflow, and thus other users, patients, family members, etc., and/or data elements, e.g., icons, panels, etc., such that these may be updated with the change information.

At 203, an embodiment communicates the change information to the appropriate application(s) in order to provide real time updates. This communication may include animation information or may be a simple identifier of the element(s) to be changed, as well as addressing information for the destination(s), e.g., mobile device identifiers, workstation identifiers, identification of a display screen in a lobby, etc.

Having an indication of a change, at 204 the recipient of the change information, e.g., a mobile application, a hospital staff work station, a display such as a television or smart TV, etc., may update the view or screen provided thereby, e.g., animate the change using this indication. This may be implemented in a variety of ways. For example, the change information communicated from the server (either via a pushing or pulling mechanism) may include animation information. Alternatively or additionally, the local (receiving) client application may have predetermined update (e.g., animation, color change, or other update information) that is triggered by the indication provided by the change information. For example, a predetermined change may be included in a template that is populated with change information, with the change to the display or view being executed in a local client action. Thus, a mobile application or web browser operating on a local (receiving) client may quickly apprise the user of the relevant change that has taken place, facilitating better management of the workflow items.

Figure 3:
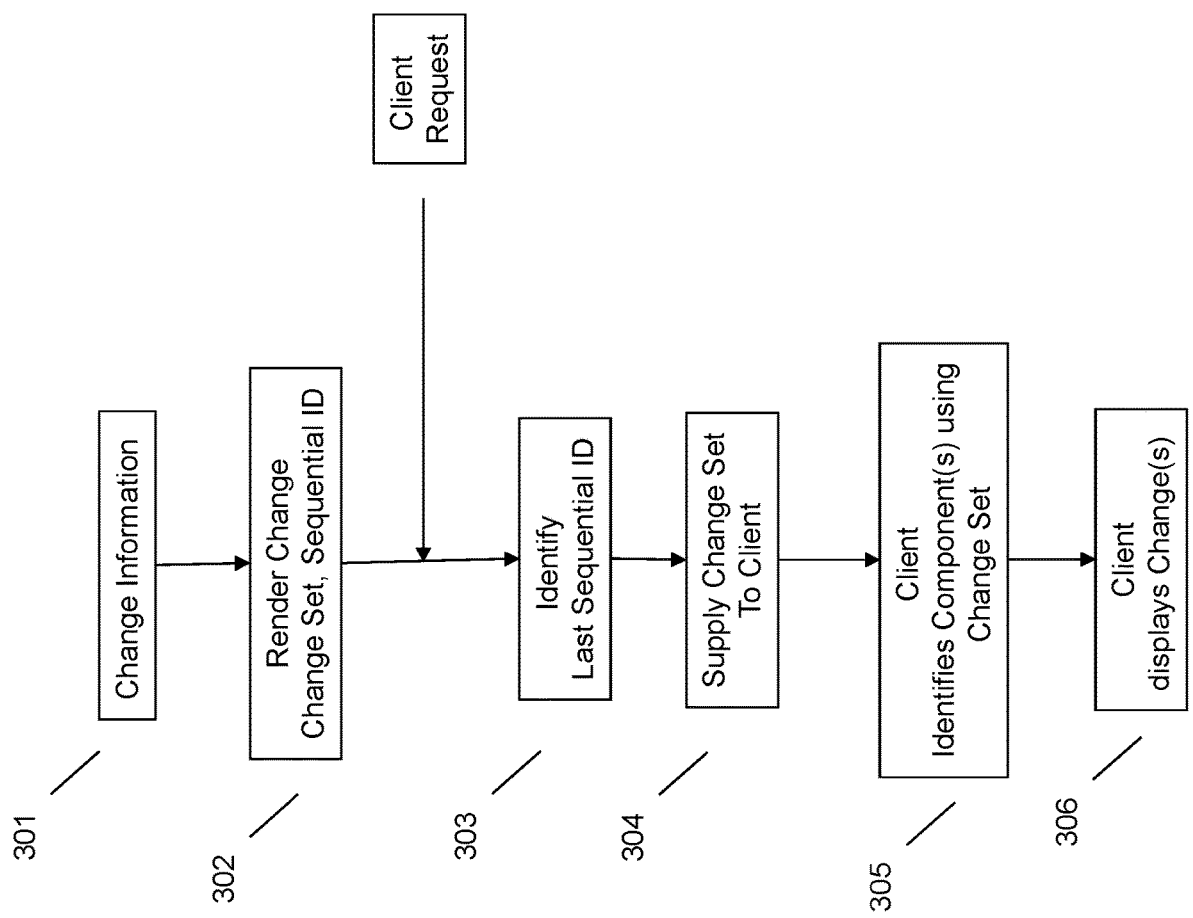
FIG. 3 illustrates an example method of preparing, communicating and implementing changes for a client screen or view.

By way of non-limiting example, and referring to FIG. 3, in an example mobile client/server implementation, the changes or workflow updates referred to herein, may be provided as follows. A universal interface virtual machine (UIVM) server (e.g., Orchestrate™ application server) receives information from the Orchestrate™ system, e.g., a server of a linked system, a workstation, a mobile client, etc., at 301. This information may be used by a UIVM server at 302 to render a change set and associate the change set with a sequential ID, which may be placed into a cache.

On an incoming request, e.g., as for example communicated by an Orchestrate™ application operating on a mobile client, a request for an updated web browser page, according to a policy (e.g., update policy), etc., the change set from UIVM server (e.g., via regular polling or when user opens application to see changes) may supply or identify the last sequence ID it received at 303.

The UIVM server may then respond at 304 with the change set required by the client to make it consistent with the underlying UIVM data store. The client may then use the change set at 305 to identify the GUI component(s) or other view components that are to be changed, and thereafter implement the changes at 306 (e.g. addition, deletion, or modification of GUI components, icons or other display graphics, etc.).

Figure 4:
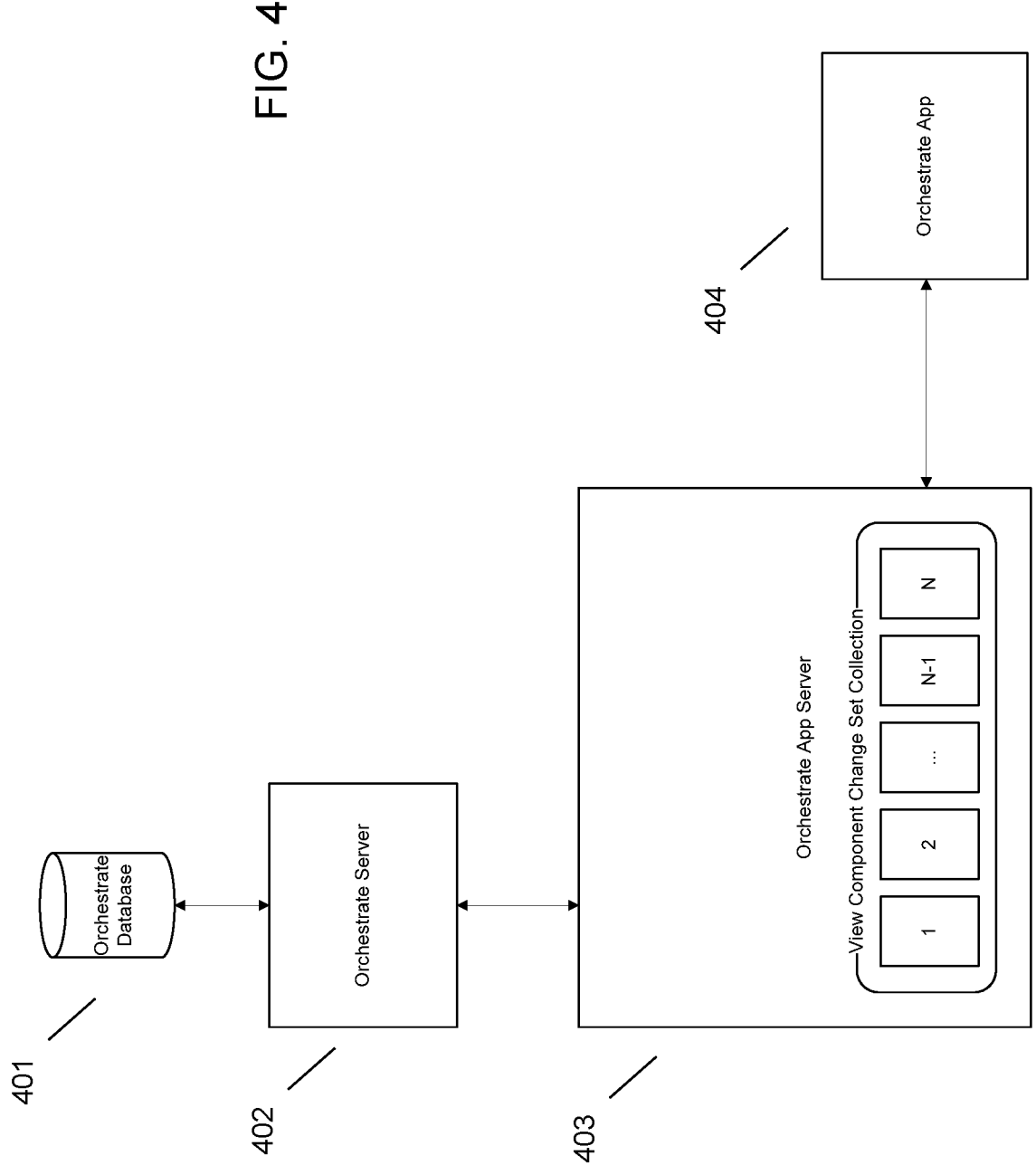
FIG. 4 illustrates an example relating to the information flow and operation of a system that communicates change information to client(s).
Figure 5:
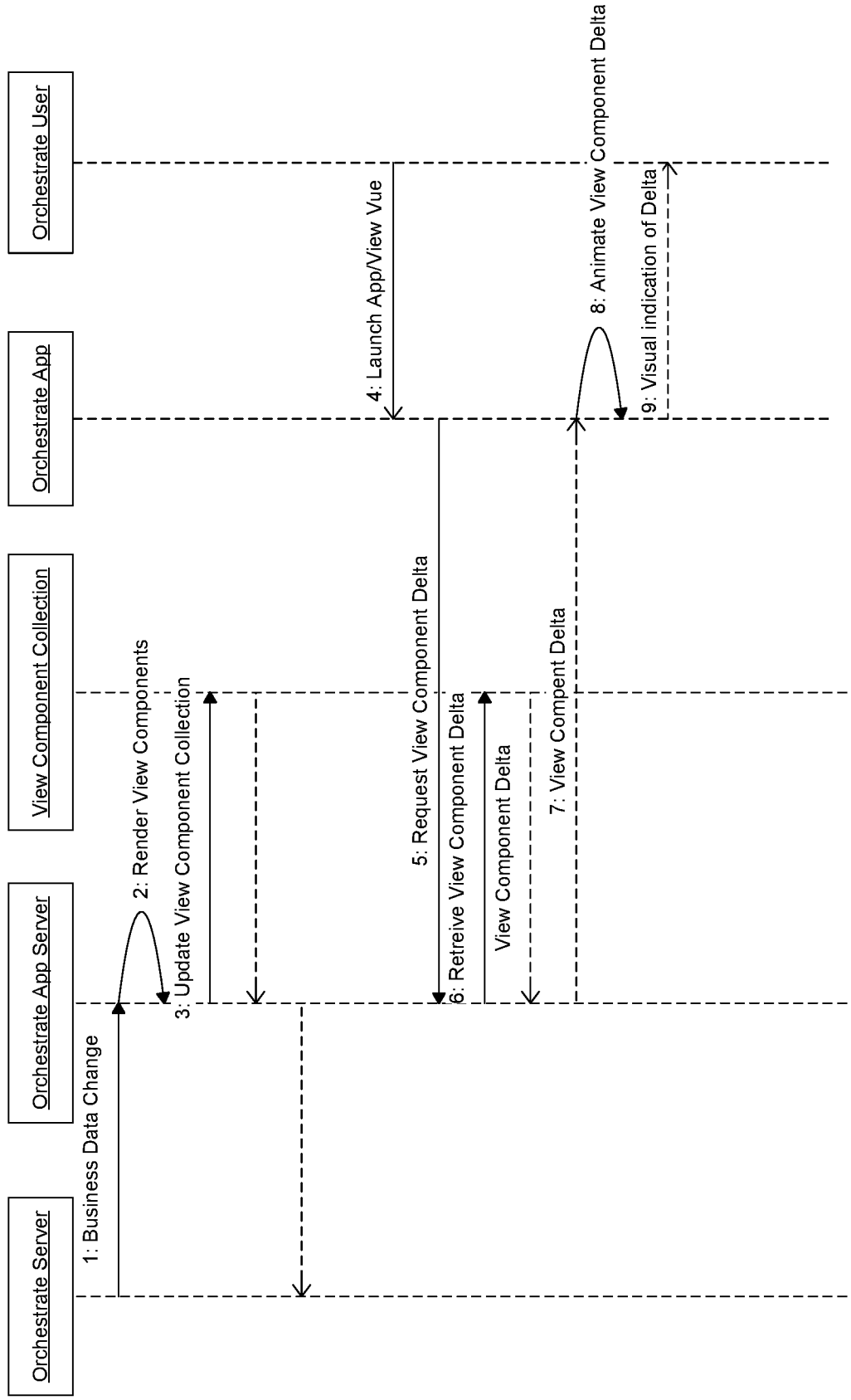
FIG. 5 illustrates an example of information flow and operation for communicating change information to clients.

Referring collectively to FIG. 4 and FIG. 5, an example embodiment is illustrated relating to the information flow and operation of a system that communicates change information to client(s), as described herein. As illustrated in this example, Orchestrate™ business data (change set) arrives at the Orchestrate™ App (application) Server (UIVM Server) 403, e.g., from the Orchestrate™ server 402. This data change set is the result of an action performed within the Orchestrate™ system or as communicated thereto, e.g., by an RTLS system, a scheduling system, etc. This data reflects the current state of the Orchestrate™ system. This data is essentially used to maintain a replicated data store of the underlying Orchestrate™ database 401.

The Orchestrate™ App Server (UIVM Server) 403 uses this information to generate the view component equivalent data consumed by the Orchestrate™ client 404 (e.g., Orchestrate App of FIG. 4). This data is the presentation equivalent (e.g., rectangle position, color, pictures, strings, etc.) of the underlying Orchestrate™ data store 401.

The Orchestrate™ App Server 403 (UIVM Server) updates the current state of the view component collection. Additionally, it records this change set. At some time, the Orchestrate™ App 404 user launches the Orchestrate™ App 404 and/or selects to view the desired Orchestrate™ view (e.g., SurgeonVue™). The Orchestrate™ App 404 requests the view component change set from the Orchestrate™ App Server 403 (UIVM Server) based on the view component change set sequence number it last received and processed.

Based on this sequence number, the Orchestrate™ App Server 403 (UIVM Server) retrieves all of the view component change sets the Orchestrate™ App 404 needs to reconcile its internal collection with the current state of the Orchestrate™ App Server's 403 internal collection. The view component delta or change is returned to the Orchestrate App 404. The Orchestrate App 404 updates its internal state and calculates the appropriate animations to perform (e.g., cell add, update, delete, etc.). A visual change such as a color change, appearance or modification of an icon, an animation, etc., may be used to draw attention to the Orchestrate App 1104 user to the change(s) made since the last time she viewed the data.

While the above description focuses on a mobile application/server implementation, in an embodiment, an application that is not integrated with the system may nonetheless access system data (and the various views or screens, as described further herein) by use of a web browser. This feature permits visibility to non-integrated systems (e.g., unmodified workstations and devices) with few requirements for compatibility (e.g., a workstation may need only to have a compatible web browser). This also permits a user of such a workstation or device to provide updates to the system, e.g., provided to the web browser interface and communicated to the central server.

For example, a user may operate within a web browser provided screen or view to communicate changes to the centrally managed system. For example, in a web browser, a notification (e.g., dialog box) appears when patients are dragged and dropped, e.g., on to a PACU screen, to alert users that placement of the patient in different screens or views or portions thereof communicates a change, e.g., moving the patient into the PACU or pre-procedure section. Users may open a second instance of the application in a second browser tab or window; allowing users to have the multiple modules open at the same time (e.g., perioperative and other clinic modules open at the same).

Users may provide various inputs, e.g., into a dedicated application or a web browser view or screen, and have these inputs communicated to a central server for updates communicated across the system. For example, in a transport dialog box, a destination field may be automatically populated by the central server with a predetermined destination when patient is scheduled for a procedure, e.g., as derived from a scheduling system data set. For example, a patient scheduled for an operation that has been admitted may be designated as destined for the preoperative area. Users may change the automatically populated information (e.g., change destination or other information to a different location) by interfacing with the screen or view, e.g., by selecting a different destination from a list in a find location dialog box.

As may be appreciated, a variety of change data may be collected and distributed by a centralized, orchestrating system and may be made use of in a variety of ways. Particular specific example embodiments are described with respect to various implementations for improving the coordination of health care workflows for various service lines.

Those having ordinary skill in the art will appreciate that the various examples provided herein are non-limiting and that other embodiments may fall within the scope of the claims.

A centralized manager, referred to herein as Orchestrate, coordinates information accessible from various sources, e.g., a scheduling system, an EMR system, client devices, an RTLS system, etc. As described herein, a scheduling system contains information that is scheduled to occur, whereas an EMR system provides records of what has happened. The centralized manager may improve the scheduling system by offering it additional data to improve the granularity of the scheduling system, e.g., providing the scheduling system with updates regarding staff availability, patient delays impacting future items in the schedule, etc. Likewise, the centralized manager may improve the quality of data in the EMR, e.g., by providing more accurate and additional information (e.g., timing information) or the like regarding procedures or events that in fact took place. By way of example, the centralized manager may enhance the value of the EMR and scheduling system by taking the anticipated schedule and tracking the patient flow and procedural process in real-time from the time the patient arrives until they are discharged or transferred, and sending detailed milestones to the scheduling system and/or the EMR system. This makes the scheduling data and the historical data more accurate in a real time fashion and makes this improved data available to enhance future performance.

Thus, a centralized system coordinates this information to enable caregivers and support staff team members, etc., the ability to anticipate and prepare for patient movement from one area to another and to plan their tasks accordingly. This approach also provides views that improve transparency and anticipation of what is next in the process. Departmental and interdepartmental communications may be improved, e.g., reducing phone calls, pages, walking around and bed holds, such that the staff an other users are apprised in real time of changes to the schedule, completion of scheduled tasks or procedures, etc. The system then delivers real time updates to the schedule as changes are made and provides accurate historical data for analysis which can be used to better estimate case times, understand and eliminate bottlenecks, determine root causes of frequent delays, and improve staff utilization.

An embodiment includes a set of screens or views designed for all stakeholders in the procedural processes (from management to housekeeping staff, family members, etc.) to communicate where a patient is at all times and what is happening as it happens. The screens share and upgrade information instantaneously across the entire system. Users can see the current patient status while management can see the entire suite and proactively address situations that may impact utilization. As will be appreciated, various views and/or versions of views may be restricted to authorized users, e.g., on the basis of login credentials and depending on the type and nature of the data contained within the screen or view.

An embodiment operates by employing templates, e.g., perioperative, procedural, clinic, and ambulatory templates, as well as other given the workflow in question. The templates include a set of standard screens or views for each module, which may be customized to be specific to the module (e.g., perioperative, pharmacy, orthopedic, cancer, heart and vascular, allergy and testing, ambulatory, infusion clinic, etc.) and/or by the user of the template (e.g., healthcare staff, management, patient family, etc.). By way of non-limiting example, a template and set of screens will be described for an example perioperative work flow.

A typical perioperative patient flow may include the following. The process starts with the day's schedule being imported to a central server, e.g., from a scheduling system. This may occur for example by an embodiment employing a batch import (e.g., ASC flat file) or a real-time HL7 interface filtered for the current day with the hospital's scheduling system. The patient appears on a roster view or screen and through this screen; management of registration and admitting may take place.

The patient may then be tracked through several views or screens (or portions thereof) as they travel through the process. The views or screens may include for example a preoperative view or screen, a procedure rooms view of screen, a post acute care unit (PACU) view or screen, a phase II (recovery) view or screen, as well as the day's anesthesia needs view or screen. Patient flow data is shared across the views or screens, e.g., as patients are moved via easy to use drag and drop functionality to different areas in a view or screen or into different views or screens. Additionally, as has been described herein, automated changes may be implemented, e.g., via RTLS data import. On such a change, e.g., a drag and drop process, the central management system may be updated such that other end clients may likewise be communicated with the retrieve or receive the change data.

Icons may graphically illustrate in the screen or view what is happening with the patient at every step of the process, e.g., displaying, changing or modifying (moving, removing, animating, etc.) of an icon may be linked with a milestone delay, completion, etc. Icons also may be used to alert and assist staff that are responsible or needed in each area. By displaying the details of what is occurring in real time, stakeholders are kept up-to-date, minimizing confusion and time wasted, e.g., with unnecessary phone calls, paging, etc. Work lists may be created to assist the staff in managing key events in the patient flow cycle. Examples of standard work lists are sterile processing or PCA requests and OR clean-up, etc.

Examples of milestones that may be monitored and utilized to communicate change data throughout the system for an example perioperative work flow are as follows. For patient arrival, a patient arrives, signs in and is admitted. The time can vary depending on if the patient was pre-registered, completed paperwork beforehand, or has special needs. Once complete, they are taken to the preoperative area. Example milestones for this phase therefore include: patient has arrived, patient is being registered, delay(s) in registering the patient, patient registration is complete, and the patient is in the preoperative waiting area (if applicable). As described herein, an embodiment uses milestones and data related thereto (e.g., completed, pending, delayed, etc.) to produce change set data that may be communicated to various client devices such that their views or screens may be updated. The views or screens may be updated via various techniques, including the use of icons or other graphics that change in color, shape, size, etc.

Once the patient is in the preoperative area, events take place before the patient moves to the OR. Thus, example milestones may include: HP & consent needed, IV started, operative site marking completed, preoperative nurse assessment needed, anesthesia needed, CRNA to see the patient, circulator to see the patient, surgeon to see the patient and give "go ahead," delay notification(s) (e.g., patient ate, PICC line required, etc.), and patient alerts. Again, various icons may be keyed to indicate in the screen or view that the milestone(s) have or have not been achieved, as well as indicating that the milestones are partially achieved, delayed or completed ahead of time, by how long, etc.

In a holding area or a transition area, often used by anesthesia to provide sedation under controlled conditions and insert arterial or central venous lines, the OR circulating nurse will meet the patient and complete an assessment and tasks. Milestones thus may include: patient is in holding area, and patient is ready for surgery.

Once the patient is in transit or has reached the OR, milestones may include: OR is setup for surgery, patient entered OR, induction needed, induction complete, positioning and preparation is complete, OR time out, incision begin, closing start, dressing applied, PACU bed needed, patient on pump, patient left OR, and OR is cleaned.

In the PACU, a patient enters and will require certain events to occur before the patient may be moved to an inpatient location or to be discharged. Accordingly, milestones may include: inpatient bed requested/assigned, anesthesia discharge, clinical discharge (patient met criteria), post operative delays, patient ready for visitors, and post operative destination assigned. In phase II (recovery) milestones may include: patient ready for visitors, patient tolerating fluids, education needed, medication needed, and patient ready for discharge.

Such milestones may be used as points at which updates within the centrally managed system are provided. For example, on reaching a predetermined milestone time, for example as programmed in the system, the fact that a milestone has not been achieved, e.g., via input interface of an end user, RTLS data, etc., the system may generate a milestone indicator, which then may be communicated to various client devices, e.g., by updating an icon display in a view or screen to show the completed milestone, its progression stage towards completion, its delay, etc.

A summary of standard screens or views included with a template, e.g., a perioperative template, may be as follows. A roster view or screen contains the schedule for the day and is used in the admitting and registration process. It depicts when the patient arrives, where he/she is, and how long they have been there. As such, the roster view or screen may be integrated with a timing function and this timing information may be used to visually display, e.g., elapsed time spent in a particular area such as an admitting and registration area.

A schedule view or screen is an electronic whiteboard or master schedule by procedural room or area. It shows the current room staffing and status as well as each patient assigned to that room with detailed information (e.g., anesthesia type, surgery type, surgery description and current patient location). This view may be accessed via an individual client device (e.g., work station, mobile device, etc.) or may be located in a central location for staff viewing, e.g., it may be displayed on device such as a dedicated monitor or smart television screen.

le;2qIn the schedule view or screen, a gap/overlap indicator or feature may be provided by an embodiment. For example, this feature displays a graphical representation of gaps and overlaps in scheduled cases on the schedule view or screen. Overlaps happen when cases are started late or take longer than anticipated and, therefore, delay the start time for the room's next scheduled case. The delay indicator may appear for example as minutes in a red cell below row representing the procedure room. Gaps happen when a case will end earlier than scheduled and will leave extra time available before the start of the room's next case. The gap may appear for example as minutes in a green cell below a row representing the procedure room. Both gaps and overlaps may be updated according to a policy, e.g., updated every minute. Staff members thus may see the coming hours of the day's schedule and make changes as necessary to keep from falling behind and to make efficient use of room availability based on real time data updates, e.g., regarding gaps and overlaps.

A staff view or screen displays staff allocation data. This or other views, e.g., schedule view or screen, room view or screen, etc., may include a staff break management feature. For example, OR charge nurses may use this as a tool to help them track lunch and rest breaks for OR staff. This feature may graphically communicate to the whole team who is currently taking breaks, who has already had lunch and rest breaks, those needing rest or lunch breaks, etc. As will be described further herein, icons displayed on the screens or views (e.g., staff view, schedule view, room view, etc.) change (e.g., change color, appear, disappear, etc.) when selected, e.g., by a staff member, to indicate that personnel are temporarily off duty or have completed a break. This visual tracking assures that every staff member gets the necessary rest time while making it easier to have adequate staffing in the procedure area at all times.

An anesthesia view or screen displays the anesthesia schedule and requirements for the day.

An incoming suite view or screen provides insight into the preoperative area. Patients appear on the incoming lists when they arrive, giving the preoperative staff advanced alerts as to their arrival and anticipated work flow. Staff can use this screen to drag and drop patients from the incoming area into the room they are in. With RTLS integration, the view or screen updates may be implemented automatically. Once placed in the preoperative area, a list of milestones may appear. For example, a display may be provided for each of the milestones to be completed and checked off before the patient moves to the procedural suite. For perioperative workflows, there also may be a PACU screen similar to the incoming suite view, e.g., a screen that shows all of the patients that are in and coming into the PACU.

A suite view or screen provides a high level view into what is happening in the entire perioperative area, preoperative, procedural room, PACU and phase II locations. This provides staff or managers with a real time summary view.

A room view or screen (e.g., OR, catheterization lab, endoscopy unit, infusion unit, etc.) is a view of an individual procedural room or unit and may be used to display and capture events and milestones as well as time stamp occurrences during a procedure. The information updates the other views or screens in real time to keep all stakeholders informed. A room view or screen also gives the procedural area the ability to communicate with staff of a unit downstream in the workflow, e.g., with the PACU, for easy hand off of the patient. For example, there may be one screen per procedural room and a touch screen device may be used to capture and communicate the information throughout the system.

A family view or screen is a HIPAA compliant view or screen that provides the patient location and status to family members, e.g., in the waiting area. As with the other views or screens, the data of the family view or screen may be displayed in a browser or application window, in a dedicated application such as a mobile application, etc., and may be automatically updated according to a policy.

An example of features of various screens or views and system functionality is as follows.

TABLE 1

System Features.

| Feature | Description | Function | Attribute |
| --- | --- | --- | --- |
| Schedule view or screen | Electronic white board of daily OR or procedural schedule with case details, case status, room status and case changes | Replaces hand written white board and shows up to the minute status of procedures, rooms and cases | Transparent, reduces errors, facilitates understanding of where resources are. More legible, fewer mistakes, and timelier updates. |
| OR Module | Adds staff assignments to schedule view or screen | Allows users to locate and account for staff at all times | Improves staff usage and allocation |
| Roster view or screen | Used to admit patients into System, record admissions tasks, display patient, staff, start times and cases, changes to same. Optional family paging included. | Shows patients that have been signed in along with procedure schedule and resources | Give admissions notification of arrivals, improves knowledge or resource allocation |
| Suite view or screen | Shows the entire suite, preop, procedure Rooms and PACU, and gives a view of current activities of the entire area. | Tracks exact status of patient within the process | Shows the entire suite, giving a quick view into the entire area to communicate what is currently happening, on screen, on screen with room occupancy, patient status, tasks, and patient milestones with time in each area. |
| Incoming Suite view or screen | Shows list of incoming patients to the Preop Area and Phase II Recovery, populated with activities based on staff input. | Shows patients that have arrived in waiting, to communicate this information to Preop Areas. Staffing boxes assigned to each room. | Reduces need for calls/paging to check status, freeing up personnel and provides timely information. Shows entire preop area with staff assignments for each room. Incoming column lists the patients that have arrived. |
| PACU view or screen | View of Recovery Suite with incoming list and view of ORs with case status, assigned recovery location | Allows recovery staff to assign beds and updates family view or screen | Reduces phone calls/paging/walk around to locate, minimizes backup in PACU. Gives family updated status, makes recovery bed location traceable and easy to locate. |
| Family view or screen | Screen for waiting room that shows all patients along with milestones and time in each. | Shows status of patients for families to see. | Improves patient satisfaction, efficiency for staff, and transparency for staff and family Reduces dependence on staff to update family members. |
| Anesthesia view or screen | Electronic white board of the days Anesthesia cases, with case details, case status, and changes to the case. | Replaces white board used to communicate anesthesia cases, with real time updates | Listing of all cases needing Anesthesia, not only in Surgical areas but hospital-wide. Provides real time knowledge of cases needing Anesthesia |
| Room view or screen | View of Procedure rooms and all activities taking place within. | Allows staff the ability to track milestones and events and communicate this information out to everyone | Provides an ability to capture milestones for the case, and other events that one would want to track. Each room view is a look into the case in order to track events and status of the case |
| OR Cleanup/Set Up | Work list showing all room cleanups and the status of those cleanup jobs. | Allows staff to better manage the room turnover process. | A work list screen used to track cleanup requests within the suite. Helps to manage the cleanup process within the suite, resulting in faster turnover and more efficiency. |
| PCA Requests | Work list showing all PCA requests within the Surgical Suite | Allows staff to track and manage PCA requests. | A work list screen used to track staff requests through the paging system. Helps to manage and track requests made in the surgical suite for assistance. |
| Sterile Processing | Work list showing Sterile Processing requests and the status of those requests until completion. | Allows staff the ability to request Sterile Processing and to follow the request until completion. | A work list used to track and manage Sterile Processing requests in the suite. |

TABLE 1-continued

System Features.

| Feature | Description | Function | Attribute |
|---------|-------------|----------|-----------|
| HL7 Interfacing | Ability to interface to scheduling and other software. | Takes schedule input to pre-populate patient information | Reduces workload on staff. Adds layer of granularity to patient scheduling. |

Beyond using an embodiment to visualize and manage procedural flow information as it is happening, an embodiment provides the ability to use the detailed information to affect future performance. An embodiment for example includes functionality to generate a set of standard reports, e.g., designed for acute care, high volume procedural areas. An embodiment allows users to extract historical data in a number of ways to understand procedural process, timing, staffing, and suite utilization. Reports can be based on the particular milestones or events that a user is interested in. An example of standard reports include:

TABLE 2

Example Standard Reports

| | Report Title | Description |
|---|---|---|
| 1 | Patient wait time | Number of minutes patients spend waiting per day/hour |
| 2 | Room turnaround time | Number of minutes the room is empty (unutilized) between procedures per day/hour |
| 3 | Room/asset utilization | Total procedure time versus clock time per day/hour per resource |
| 4 | Case minutes | Total procedure time per day/hour |
| 5 | No shows | Number of patients with scheduled procedures that did not show up for the appointment per day |
| 6 | Patient arrival vs. scheduled start | Minutes before the scheduled start that the patient first arrives in service (waiting, registration, or directly into room) |
| 7 | Cancelled procedures | Total number of cancelled procedures per day |
| 8 | Actual vs. scheduled start | Minutes before the scheduled time that the procedure is recorded as started per day/hour |
| 9 | Case volume | Total number of procedures per day/hour |
| 10 | Registration time by registrar | Average registration time per patient by registrar per day/hour |
| 11 | Registration time | Average registration time per patient per day/hour |
| 12 | Enter preop vs. scheduled start | Minutes before scheduled start that the patient arrives in Preoperative area |
| 13 | Surgeon check in vs. scheduled start | Minutes before the scheduled start time that the surgeon checks in for the case by surgeon |
| 14 | Surgeon check in vs. scheduled start-first start only | Minutes before the scheduled start time that the surgeon checks in for the case by surgeon |
| 15 | Anesthesiologist check in vs. scheduled Start | Minutes before scheduled start that the anesthesiologist signals preop go ahead |
| 16 | RN ready vs. scheduled start | Minutes before scheduled start that the RN signals preop go ahead |
| 17 | Preop patient ready vs. scheduled start | Minutes before scheduled start that the all preop activities are complete |
| 18 | Cleanup start vs. patient left OR | Minutes after previous case left the OR that cleanup started |
| 19 | Setup complete vs. scheduled start | Minutes before the scheduled start that the setup for the case was complete |
| 20 | Clinically ready to leave PACU vs. PACU leave | Minutes from Clinical Discharge until patient leaves PACU per patient per day/hr |
| 21 | Request PACU after closing start | Minutes from closing start until a PACU bed request per pat per day/hr |
| 22 | Assign PACU after PACU request | Minutes from PACU bed request until PACU bed assignment per patient per day/hr |
| 23 | Case delay duration by case delay | Minutes from start to complete for each case delay reason per patient per day/hr (user defined list of reason codes) |
| 24 | Case delay frequency by case delay reason | Count of case delays occurrences for each case delay reason per patient per day/hr | data compiled by or accessible to the centralized system are apparent. For example, if a user selects a report regarding on-time starts for a particular procedure, unit or area, an embodiment may produce a percentage and count for all cases that start on-time or vice versa.

An embodiment is positioned as a centralized service and provides interface capability with hospital/clinic scheduling and clinical systems for an integrated platform to optimize efficiency in procedural care areas. An embodiment may for example utilize HL7 standards as a common framework for integration with external systems. Scheduling messages sent In an embodiment, reports may be integrated with the information available to the central server. For example, if a user selects a zone in a screen or view (e.g., from a zone list or like GUI element), a report of interest (e.g., delay time) may be automatically generated for that zone selected. Reports may be generated such that patterns in the historical to an embodiment may include new, modified, and rescheduled cases as well as appointment cancellations. Scheduling information may be used to populate an embodiment database with the current day's schedule and this data store may be updated throughout the day, e.g., based on messages from the hospital/clinic scheduling system. Scheduled appointments for future dates may be stored and presented on the appropriate day within the various views or screens, as described herein.

An embodiment may also send and receive information, e.g., via HL7 messages, for specific real-time events, for example including procedure room milestones and patient movement in the procedural care areas. If a facility has an existing information system or RTLS service with patient flow data available, an embodiment may be used to improve the granularity or detailed milestones of the existing modules. For example, even if an existing system does have a procedural flow capability, it may not be integrated across the whole facility and have access to various systems, thereby only providing limited value. Additionally, existing systems do not have the reporting and scheduling capability to use the existing data, e.g., for longer term improvements.

An embodiment may be integrated with an existing patient management system to automatically match patients and eliminates duplication of patient records, allowing for importing of new patients from procedural areas and updating between the central system and the existing patient management system. An embodiment allows a user to initiate, update and review bed requests pending in a patient management system for procedural patients from within a standard template of views provided by an embodiment. For example, inpatient bed status from an existing patient management system may be communicated to an embodiment acting as a coordinator and thus be displayed in a view or screen such that the procedural area staff viewing the view or screen knows where the patient is before the procedure and where the patient will go after the procedure, helping to improve transport functions and minimize backups in the PACU.

As may be appreciated, an embodiment providing the screens or views also facilitates use of the screen or view functionality to populate and communicate changes within the system. For example, a user may implement a change in a view or screen that is used by an embodiment to automatically activate placement requests in connected, existing bed management system, e.g., upon schedule import or at the time a patient is added on to the schedule. An embodiment also provides details on procedural status and notification of cancelled procedures. Added communication for example helps to improve procedural utilization by ensuring fill-in procedures are conducted in a timely manner and patients can be expeditiously returned to their beds, reducing waiting and bottlenecks in a procedural area.

An embodiment allows for viewing an updating patient attributes and isolations (e.g., alerts) recorded in an existing patient management system. This improves safety by ensuring procedural staff is aware of a patient's condition or attributes.

Procedure status and details recorded in a centralized manager are therefore accessible from within other connected systems, providing increased communication, e.g., to nursing units. This permits staff such as nursing units interfacing with an existing patient management system to be apprised of the when, what and where of upcoming procedures, the historical view of a patient's procedures during his/her hospital stay, current status of a patient in an area (e.g., in the OR) and have access to communication functionality across the connected systems, e.g., a call to OR feature may be linked by an embodiment to various other existing systems to improve communication of transportation needs, etc.

To take automation even further, an embodiment may be integrated with an RTLS to automate the manual progression of location based milestones (e.g., automate a "drag and drop" function performed by staff in a screen or view), such as patient moves. RTLS integration may reduce manual intervention and eliminate errors, increase compliance within the system, decrease delays, and provide accurate time stamps of events automatically. As may be appreciated, this frees staff to focus on the job at hand.

RTLS integration provides improved workflow by automatically detecting patient or asset location and triggering milestones, eliminating manual updates and reduced the potential for human error. Additionally, automated patient location and movement of staff, patients and equipment resources may be communicated throughout the system, e.g., by a central manager communicating updates automatically, e.g., via change set data distributed to a requesting client device.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

Any combination of one or more non-signal device readable storage medium(s) may be utilized. A storage medium may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage medium is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a special purpose information handling device or other programmable data processing device to produce a machine, such that the instructions, which execute via a processor of the device implement the functions/acts specified.

It is worth noting that while specific blocks (or other illustrated elements or text) are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. A method, comprising:
    identifying a presence of a patient in a location, wherein the location is associated with at least a preoperative area;
    receiving, at a server and based on the identified location, change data from a mobile device, wherein the change data comprises a patient progress indicator as the patient completes a predetermined listing of milestone events, wherein each milestone event in the predetermined listing is associated with a medical routine and wherein the predetermined listing is particular to the location;
    identifying, using a processor, a set of display elements impacted by the change data;
    updating, using the processor, the set of display elements according to the change data, wherein the updating comprises updating the set of display elements each time a milestone event is completed;
    storing, in a memory device, a sequential identification associated with the updated set of display elements;
    receiving, at the server, a request from an end user client for updated information, wherein the request includes a previous sequential identification;
    determining, using the processor, a delta representing the difference between the sequential identification and the previous sequential identification;
    determining a relationship between a user of the end user client and the patient, wherein the relationship corresponds to one of: a health-care provider and a family member;
    generating, using the processor and based at least in part on the determined relationship, a set of updated view components for the end user client based on the delta, wherein the set of updated view components is more expansive for the health-care provider than the family member; and
    communicating, over a network connection, the set of view components to the end user client.

2. The method of claim 1, wherein the set of view components comprise data for updating display elements of an end user application display running on the end user client.

3. The method of claim 2, wherein the mobile device and the end user client run the at least two different end user application displays.

4. The method of claim 3, wherein the at least two different end user application displays are associated with different times of a single, larger workflow.

5. The method of claim 1, wherein the mobile device is a radio frequency identification (RFID) tracking device.

6. The method of claim 5, wherein the change data comprises real time location data derived from the RFID tracking device.

7. The method of claim 1, wherein the end user client comprises a mobile device.

8. The method of claim 1, wherein the request is received via a wireless communications network.

9. The method of claim 8, wherein the request from the end user client for updated information is generated automatically on waking of the end user client.

10. The method of claim 1, wherein the memory device comprises a repeatedly updated cache memory.

11. A system, comprising:
    an application server comprising a memory device; and
    a network communication device;
    said server including a processor configured to:
    identify a presence of a patient in a location, wherein the location is associated with at least a preoperative area;
    receive change data from a mobile device, wherein the change data comprises a patient progress indicator as the patient completes a predetermined listing of milestone events, wherein each milestone event in the predetermined listing is associated with a medical routine and wherein the predetermined listing is particular to the location;
    identify a set of display elements impacted by the change data;
    update the set of display elements according to the change data, wherein the updating comprises updating the set of display elements each time a milestone event is completed;
    store, in the memory device, a sequential identification associated with the updated set of display elements;
    receive a request from an end user client for updated information, wherein the request includes a previous sequential identification;
    determine a delta representing the difference between the sequential identification and the previous sequential identification;
    determine a relationship between a user of the end user client and the patient, wherein the relationship corresponds to one of: a health-care provider and a family member;
    generate, based at least in part on the determined relationship, a set of updated view components for the end user client based on the delta, wherein the set of updated view components is more expansive for the health-care provider than the family member; and
    communicate, using the network communication device, the set of view components to the end user client.

12. The system of claim 1, wherein the set of view components comprise data for updating display elements of an end user application display running on the end user client.

13. The system of claim 12, wherein the mobile device and the end user client run the at least two different end user application displays.

14. The system of claim 13, wherein the at least two different end user application displays are associated with different times of a single, larger workflow.

15. The system of claim 11, wherein the mobile device is a radio frequency identification (RFID) tracking device.

16. The system of claim 15, wherein the change data comprises real time location data derived from the RFID tracking device.

17. The system of claim 11, wherein the end user client comprises a mobile device.

18. The system of claim 11, wherein the request is received via a wireless communications network.

19. The system of claim 18, wherein the request from the end user client for updated information is generated automatically on waking of the end user client.

20. A program product, comprising:
a storage device having code stored therein that is executable by a processor, the code comprising:
code that receives a presence of a patient in a location, wherein the location is associated with at least a preoperative area;
code that receives, at a server, change data from a mobile device, wherein the change data comprises a patient progress indicator as the patient completes a predetermined listing of milestone events, wherein each milestone event in the predetermined listing is associated with a medical routine and wherein the predetermined listing is particular to the location;
code that identifies, using the processor, a set of display elements impacted by the change data;
code that updates, using the processor, the set of display elements according to the change data, wherein the code that updates comprises code that updates the set of display elements each time a milestone event is completed;
code that stores, in a memory device, a sequential identification associated with the updated set of display elements;
code that receives, at the server, a request from an end user client for updated information, wherein the request includes a previous sequential identification;
code that determines, using the processor, a delta representing the difference between the sequential identification and the previous sequential identification;
code that determines a relationship between a user of the end user client and the patient, wherein the relationship corresponds to one of: a health-care provider and a family member;
code that generates, using the processor and based at least in part on the determined relationship, a set of updated view components for the end user client based on the delta, wherein the set of updated view components is more expansive for the health-care provider than the family member; and
code that communicates, over a network connection, the set of view components to the end user client.

* * * * *